United States Patent [19]

Abele et al.

[11] Patent Number: 5,071,943
[45] Date of Patent: Dec. 10, 1991

[54] PROCESS FOR THE ISOLATION OF TETRACHLOROBUTANE AND FOR THE PRODUCTION OF PHENOLIC RESINS FROM MIXTURES OF CHLORINE-SUBSTITUTED HYDROCARBONS

[75] Inventors: Manfred Abele, Cologne; Hans-Josef Buysch, Krefeld; Michael Happ, Dormagen; Werner Obrecht, Moers; Heinrich Schrage; Hugo Vernaleken, both of Krefeld, all of Fed. Rep. of Germany

[73] Assignee: Bayer Aktiengesellschaft, Leverkusen, Fed. Rep. of Germany

[21] Appl. No.: 655,716

[22] Filed: Feb. 15, 1991

[30] Foreign Application Priority Data

Feb. 27, 1990 [DE] Fed. Rep. of Germany ....... 4006129

[51] Int. Cl.$^5$ ............................................. C08G 63/78

[52] U.S. Cl. ................................. 528/205; 528/159; 528/212; 528/86
[58] Field of Search ................................ 528/205, 159

[56] References Cited

U.S. PATENT DOCUMENTS 3,644,537  2/1972  Dannels et al. ...................... 528/205
3,752,780  8/1973  Petersen et al. ..................... 528/159
4,707,526 11/1987  Sasaki et al. ......................... 528/205

Primary Examiner—John Kight, III
Assistant Examiner—John Cooney
Attorney, Agent, or Firm—Connolly and Hutz

[57] ABSTRACT

Secondary products formed in the chlorination of butadiene can be reacted with phenols in the absence of iron catalysts to form novolak-like phenolic resins in such a way that the tetrachlorobutane present in the secondary products does not react. It can be distilled off with the excess phenol and isolated in pure form from the distillate obtained.

6 Claims, No Drawings

PROCESS FOR THE ISOLATION OF TETRACHLOROBUTANE AND FOR THE PRODUCTION OF PHENOLIC RESINS FROM MIXTURES OF CHLORINE-SUBSTITUTED HYDROCARBONS

This invention relates to a process by which novolak-like phenolic resins can be produced from mixtures of at least partly chlorine-substituted $C_{4-8}$ hydrocarbons containing inter alia 1,2,3,4-tetrachlorobutane by reaction with phenols in such a way that the 1,2,3,4-tetrachlorobutane does not react and can be isolated. In this way, by-products of the type formed, for example, in the chlorination of butadiene can be worked up to two completely different, valuable products, thus eliminating the need for the hitherto usual disposal by burning.

It is known that novolaks are fusible, non-self-curing polyphenols of which the aromatic nuclei are attached by alkylidene groups and which are soluble in a number of organic solvents. They may be produced from phenols and keto compounds in the presence of acidic catalysts, a molar ratio of keto compound to phenol of at most 1 and preferably of most 0.75 normally being maintained: cf. "Methoden der Organischen Chemie" (Houben-Weyl), Vol. 14/2, Georg Thieme Verlag, Stuttgart 1963, pages 193 et seq.

In the context of the present invention, "novolak-like phenolic resins" are understood to be phenolic resins of which the linking members are not confined to alkylidene groups, but which are substantially free from groups capable of self-crosslinking, i.e. primarily hydroxymethyl groups.

In addition to chloroprene, unwanted secondary products containing 4 to 8, preferably 4 or 8, carbon atoms and at least 3, preferably at least 4, functional groups from the series consisting of chlorine atoms and $C=C$ double bonds are formed during the production of chloroprene by chlorination of butadiene. Typical secondary products consist of mixtures of 20 to 60% by weight 1,2,3,4-tetrachlorobutane, 10 to 60% by weight dichlorooctadienes, 3 to 20% by weight trichlorobutenes, 2 to 8% by weight tetrachlorooctenes and up to 15% by weight dichlorobutenes, dichlorobutanes and hexachlorooctanes. The individual components cannot be cleanly separated from these mixtures by distillation on account of the closeness of their boiling points. For this reason, the secondary products have not hitherto been put to any use, but instead have been burnt. This is a serious disadvantage, particularly in view of the 1,2,3,4-tetrachlorobutane present in the mixture of secondary products, because the dehydrochlorination of this product leads to 2,3-dichlorobutadiene - an important comonomer for the synthesis of polychloroprene.

Accordingly, the problem addressed by the present invention was to find a way of isolating the 1,2,3,4-tetrachlorobutane in pure form from the described mixture and to avoid the economically and ecologically undesirable incineration of the less valuable components and to convert these components into more valuable products.

It has now surprisingly been found that the described secondary products can be reacted with phenols to form novolak-like phenolic resins in such a way that all the components except for the 1,2,3,4-tetrachlorobutane react. The remaining tetrachlorobutane may be separated by distillation, together with excess phenol and any solvent used, and recovered from the distillate obtained by fractional distillation. It may then be used without further purification as a starting material for the production of 2,3-dichlorobutadiene. Irrespective of its heterogeneous constituents, the phenolic resin remaining as residue may be used, for example as a reinforcing component in rubber compounds to be vulcanized, without any need for expensive purification steps.

Although the reaction of unsaturated hydrocarbons with phenols to phenolic resins was known from U.S. Pat. No. 3,644,537, the problem to be solved in that case was not to isolate 1,2,3,4-tetrachlorobutane from complex mixtures of chlorinated hydrocarbons and to react the other components of the mixtures.

Accordingly, the present invention relates to a process for the isolation of 1,2,3,4-tetrachlorobutane and for the production of novolak-like phenolic resins by reaction of A) phenols with B) mixtures of at least partly chlorine-substituted $C_{4-8}$ hydrocarbons containing 1,2,3,4tetrachlorobutan in the absence of effective quantities of iron catalysts, after which the phenolic resin is separated from the remaining 1,2,3,4-tetrachlorobutane, excess phenol and any solvent used by methods known per se on completion of the alkylation reaction.

The above-described mixtures of chlorinated hydrocarbons appear advantageous for the process according to the invention when their content of 1,2,3,4-tetrachlorobutane is at least 10% by weight and preferably at least 20% by weight, based on the mixture. The chlorine content of the mixtures B is generally 40 to 70% by weight and preferably 45 to 60% by weight, based on mixture B.

Preferred phenols A for the process according to the invention include monohydric and dihydric mononuclear phenols which, apart from the phenolic hydroxyl groups, contain no other substituents, such as unsubstituted phenol itself, pyrocatechol, resorcinol, hydroquinone; monohydric $C_{1-6}$ alkylphenols, such as cresols, xylenols, ethylphenols, hexylphenols; monohydric phenylphenols, such as hydroxy biphenyls; mononuclear and binuclear $C_{6-18}$ bisphenols, such as dihydroxybiphenyls, bis-(4-hydroxyphenyl)-hydroxymethane, 2,2-bis-(4-hydroxyphenyl)-propane and bis-(4-hydroxyphenyl)-sulfide.

In the process according to the invention the starting products are generally used in quantities corresponding to an equivalent ratio of phenolic OH to functional groups of the secondary product components (chlorine or $C=C$ double bond) of 1:10 to 10:1, preferably 1:4 to 8:1 and, more preferably, 1:2 to 5:1.

Preferred iron catalysts, which are not to be used in effective quantities for the process according to the invention because they catalyze the reaction of 1,2,3,4-tetrachlorobutane with phenols, include metallic iron and compounds of iron, preferably divalent and trivalent iron, such as for example the bromides, nitrates, sulfates, oxalates and, more particularly, the chlorides. The effective quantity is generally from 0.05 to 10% by weight and preferably from 0.1 to 3% by weight, based on the mixtures of hydrocarbons B used.

Suitable catalysts for the process according to the invention include any chemical compounds which accelerate Friedel-Crafts alkylations (except for iron catalysts, see above), i.e. protonic acids and Lewis acids such as, for example, sulfuric acid, hydrogen chloride, phosphoric acid, aluminium chloride, tin chloride, boron trifluoride, titanium tetrachloride, zinc chloride and zinc sulfate. Zinc salts are preferred; zinc sulfate is particularly preferred. The reaction may even be carried out in the absence of a catalyst because the hydrogen chloride formed during the reaction also has a catalytic effect.

In the case of salts, typical quantities of catalyst are generally from 0.05 to 10% by weight and preferably from 0.1 to 3% by weight. In the case of acids, typical quantities of catalyst are generally from 0.05 to 10% by weight and preferably from 0.1 to 5% by weight, based on mixture B.

The process according to the invention is preferably carried out in the absence of solvents. However, organic solvents that are inert under the reaction conditions, preferably those having a boiling point above 120° C. and more particularly above 180° C., such as nitrobenzene, dichlorobenzenes, benzonitrile, chloronaphthalenes, may readily be used. If it is desired to carry out the process in solution, the organic solvent will be used in quantities of 5 to 100% by weight, based on the sum of phenol A and mixture B.

The process according to the invention is exothermic and, accordingly, proceeds on its own in the absence of heat applied from outside once it has been started. To obtain a substantially complete reaction and, hence, a minimal chlorine content in the end product, it may be advisable to leave the reaction mixture standing for 2 to 20 hours at temperatures of 40 to 280° C., preferably at temperatures of 80 to 250° C. and more preferably at temperatures of 120 to 200° C. after the components have been added. The reaction is over when the evolution of hydrogen chloride stops.

In practice, the process according to the invention may be carried out, for example, by initially introducing the molten phenol A and the catalyst and adding the mixture B, optionally dissolved in the organic solvent. To obtain thorough mixing of the components, the reaction mixture may be stirred. On completion of the reaction, solvent (where present) and excess phenol may be removed, preferably by distillation, optionally under reduced pressure. The tetrachlorobutane may be recovered directly or from the distillate obtained by methods known per se, for example by fractional distillation. The excess phenol removed may be reused for further reactions, optionally in admixture with any solvent used.

The phenolic resins produced in accordance with the invention contain 0.2 to 1 and preferably 0.4 to 0.8 mol units emanating from mixture B per mol unit emanating from phenol A.

The phenolic resins produced in accordance with the invention generally have softening points (according to DIN 53 244) in the range from 50 to 200° C., OH values in the range from 100 to 550 and number average molecular weights $\overline{M}_n$ in the range from 250 to 2000 (as determined by vapor pressure osmometry in methanol and acetone, the lower value being regarded as the correct value).

The phenolic resins produced in accordance with the invention are suitable as a reinforcing resin component for rubber compounds to be vulcanized. These rubber compounds may be based on natural and synthetic rubbers.

Preferred synthetic rubbers are described, for example, in W. Hoffmann, Kautschuk-Technologie, Gentner Verlag, Stuttgart 1980, and include inter alia BR—polybutadiene
ABR—butadiene/alkyl $C_{1-4}$ acrylate copolymers having acrylate contents of 5 to 60 and preferably 15 to 50% by weight
CR—polychloroprene
IR—polyisoprene
IIR—isobutylene/isoprene copolymers
SBR—styrene/butadiene copolymers having styrene contents of 1 to 60 and preferably 20 to 50% by weight
NBR—butadiene/acrylonitrile copolymers having acrylonitrile contents of 5 to 60 and preferably 10 to 50% by weight
EPDM—ethylene/propylene/diene copolymers and mixtures of these rubbers. The rubbers to be used for the process according to the invention have glass transition temperatures below 20° C. and preferably below 0° C., as determined by the torsion pendulum test according to DIN 53 445. The dosage of the phenolic resins may be from 1 to 50 and preferably from 3 to 15% by weight, based on rubber.

Since the phenolic resins produced in accordance with the invention are not self-curing, they require the addition of formaldehyde, formaldehyde donors, such as hexamethylene tetramine, or melamine or urea condensates containing methylol groups for curing, these curing agents generally being used in quantities of from 2.5 to 50% by weight and preferably in quantities of 5 to 15% by weight, based on phenolic resin. If the phenolic resins are cured and the rubber surrounding them is vulcanized, it may be assumed that crosslinked systems along the lines of so-called interpenetrating networks are formed. In that case, it may be assumed that the phenolic resin produced in accordance with the invention is not part of the vulcanizing system required for the rubber.

The use of these resin systems in rubber compounds leads to improvements in certain important mechanical properties of the vulcanizates produced therefrom, including for example hardness and modulus values. The reinforcing resins may be incorporated by means of the units typically used for the production of rubber mixtures, including for example internal mixers and mixing rolls. At high mixing temperatures (internal mixer), the reinforcing resin and the curing component should be separately incorporated to avoid premature reactions and to obtain high vulcanizate hardness. It is advisable in this regard to incorporate the curing component at a low mixing temperature (max. approx. 100° C.) towards the end of the preparation of the mixture.

The resins according to the invention may be used for the production of industrial rubber products, for example rollers, seals, floor coverings.

In the following Examples, percentages and parts are by weight.

EXAMPLES

The "product mixture" referred to in the following Examples is understood to be a mixture of secondary products obtained in the chlorination of butadiene with a chlorine content of 54% and a C=C double bond content of 0.575 equivalents per 100 g product. 35% of the product mixture consisted of tetrachlorobutane, 40% of dichlorooctadienes, 7% of trichlorobutenes, 8% of trichlorooctenes and 10% of other products in relatively small amounts.

EXAMPLE 1

200 g product mixture were added dropwise at 60° C. to a melt of 200 g phenol and 2 g anhydrous zinc sulfate, the reaction mixture undergoing a spontaneous increase in temperature to approximately 80° C. The reaction mixture was then heated for 6 hours at 182° C. and the tetrachlorobutane was distilled off together with excess phenol. 179 g of the phenolic resin softening at 98° C., OH value 215, were left as residue.

In addition to 106 g of a phenol/tetrachlorobutane mixture (94:6 parts), fractional distillation of the distillate obtained at normal pressure produced 64 g pure tetrachlorobutane.

EXAMPLE 2

200 g product mixture were added dropwise at 60° C. to a melt of 200 g phenol, the reaction mixture undergoing a spontaneous increase in temperature to approximately 80° C. The reaction mixture was then heated for 8 hours at 182° C. and the tetrachlorobutane was distilled off together with excess phenol. 165 g of the phenolic resin softening at 70° C., OH value 158, were left as residue.

In addition to 127 g of a phenol/tetrachlorobutane mixture (94:6 parts), fractional distillation of the distillate obtained at normal pressure produced 62 g pure tetrachlorobutane.

EXAMPLE 3

200 g product mixture were added dropwise at 60° C. to a melt of 200 g phenol and 2 g tin tetrachloride, the reaction mixture undergoing a spontaneous increase in temperature to approximately 80° C.

The reaction mixture was then heated for 6 hours at 182° C. and the tetrachlorobutane was distilled off together with excess phenol. 179 g of the phenolic resin softening at 88° C., OH value 215, were left as residue.

In addition to 106 g of a phenol/tetrachlorobutane mixture (94:6 parts), fractional distillation of the distillate obtained at normal pressure produced 64 g pure tetrachlorobutane.

EXAMPLE 4

200 g product mixture were added dropwise at 60° C. to a melt of 400 g phenol and 4 g chromium chloride, the reaction mixture undergoing a spontaneous increase in temperature to approximately 80° C. The reaction mixture was then heated for 6 hours at 182° C. and the tetrachlorobutane was distilled off together with excess phenol. 214 g of the phenolic resin softening at 69° C., OH value 240, were left as residue.

In addition to 283 g of a phenol/tetrachlorobutane mixture (94:6 parts), fractional distillation of the distillate obtained at normal pressure produced 53 g pure tetrachlorobutane.

APPLICATION

The object of the following test is to illustrate the accordance with the use of the phenolic resins produced in invention as reinforcing resins for rubber compounds and vulcanizates produced therefrom.

The following test mixture produced in two stages was used for this purpose. The first phase of the production process was carried out in an internal mixer (kneader). The following constituents were mixed (in parts):

| | |
|---|---|
| Natural rubber (type SMR 5) | 75.0 |
| Polybutadiene | 25.0 |
| Stearic acid | 2.0 |
| Zinc oxide | 5.0 |

| -continued | |
|---|---|
| Reinforcing resin (cf. Table) | 7.5 |
| Carbon black N 326 | 70.0 |
| N-Isopropyl-N'-phenyl-p-phenylene-diamine (IPPD) | 1.5 |
| 2,2,4-Trimethyl-1,2-dihydroquinoline, polymerized (TMQ) | 1.0 |
| | 187.0 |

After a mixing time of 5 minutes, the internal kneader was emptied and the mixture thus prepared was mixed to completion on following mixing rolls in accordance with the following formulation (in parts):

| | |
|---|---|
| Preliminary mixture | 187.0 |
| Sulfur | 2.5 |
| Benzothiazyl-2-sulfene morpholide | 1.5 |
| N-cyclohexylthiophthalimide | 0.3 |
| Hexamethylene tetramine | 0.76 |

The final mixtures were vulcanized for 30 minutes at 150° C.

The results of the vulcanizate tests are shown in the following Table. The results of the vulcanizate tests show that the resins produced in accordance with the invention have an excellent reinforcing effect.

| Vulcanizates reinforced with various resins | | |
|---|---|---|
| Test | Comparison, vulcanizate free from reinforcing resin | Resin of Example 1 |
| Tensile strength (Mpa) | 19.4 | 14.2 |
| Elongation at break (%) | 332 | 290 |
| Modulus at 100% Elongation (Mpa) | 4.4 | 5.2 |
| Hardness (Shore A) | | |
| at 23° C. | 77 | 90 |
| at 70° C. | 72 | 88 |
| Rebound resilience (%) determined at | | |
| 23° C. | 43 | 38 |
| 70° C. | 53 | 43 |

We claim:

1. A process for the isolation of 1,2,3,4-tetrachlorobutane and for the production of novolak-like phenolic resins by reaction of A) phenols with B) mixtures of at least partly chlorine-substituted $C_{4-8}$ hydrocarbons containing 1,2,3,4-tetrachlorobutane in the absence of effective quantities of iron catalysts, after which the phenolic resin is separated from the 1,2,3,4-tetrachlorobutane, excess phenol and any solvent used by methods known per se on completion of the alkylation reaction.

2. A process as claimed in claim 1, in which the secondary products obtained in the chlorination of butadiene are used as mixture B).

3. A process as claimed in claim 1, in which zinc sulfate is used as the catalyst.

4. A process as claimed in claim 1, in which components A and B are used in an equivalent ratio of phenolic OH to functional groups of mixture B of 1:10 to 10:1.

5. A process as claimed in claim 1, in which the reaction temperature is 40 to 280° C.

6. A process as claimed in claim 1, in which the tetrachlorobutane is recovered from the distillate containing excess phenol, tetrachlorobutane and, optionally, solvent by fractional distillation.

* * * * *